(12) United States Patent
Lo

(10) Patent No.: US 9,381,074 B2
(45) Date of Patent: Jul. 5, 2016

(54) DECIDUOUS TEETH STORAGE DEVICE

(71) Applicant: Chiu-Mei Lo, Hsinchu (TW)

(72) Inventor: Chiu-Mei Lo, Hsinchu (TW)

( * ) Notice: Subject to any disclaimer, the term of this patent is extended or adjusted under 35 U.S.C. 154(b) by 0 days.

(21) Appl. No.: 14/794,812

(22) Filed: Jul. 9, 2015

(65) Prior Publication Data

US 2016/0095683 A1     Apr. 7, 2016

(30) Foreign Application Priority Data

Oct. 3, 2014   (TW) .............................. 103217634 U

(51) Int. Cl.
*A61C 19/10*     (2006.01)
*A47B 88/04*     (2006.01)
*A47B 81/00*     (2006.01)

(52) U.S. Cl.
CPC ............... *A61C 19/10* (2013.01); *A47B 81/00* (2013.01); *A47B 88/04* (2013.01)

(58) Field of Classification Search
USPC ................................................... 206/83, 485
See application file for complete search history.

(56) References Cited

U.S. PATENT DOCUMENTS

| | | | | |
|---|---|---|---|---|
| 2,363,997 A * | 11/1944 | Rothman | ............... | A61C 19/10 206/83 |
| 2,705,815 A * | 4/1955 | Brauer | ................ | A61C 13/00 206/83 |
| 3,111,760 A * | 11/1963 | Semmelman | .......... | A61C 19/10 206/83 |
| 4,694,956 A * | 9/1987 | Sims | .................... | A61C 19/008 206/527 |
| 4,697,700 A * | 10/1987 | Weissman | .......... | A61C 13/0027 206/467 |
| 4,775,318 A * | 10/1988 | Breslin | .................. | A61C 19/10 206/63.5 |
| 4,923,058 A * | 5/1990 | Dennison | ............... | A63H 33/00 206/564 |
| 5,621,990 A * | 4/1997 | Blanchard | ............ | A61C 19/008 206/83 |
| 6,082,531 A * | 7/2000 | Hazenbos | ............ | A61C 19/008 206/63.5 |
| 6,932,213 B1 * | 8/2005 | Distad | .................. | A61C 19/008 206/232 |
| 2012/0073996 A1 * | 3/2012 | Arnold | ................. | A61C 19/008 206/83 |

* cited by examiner

*Primary Examiner* — Jacob K Ackun

(74) *Attorney, Agent, or Firm* — Leong C. Lei

(57) ABSTRACT

The deciduous teeth storage device contains an openable casing, an upper gum cast, a lower gum cast, and a number of artificial teeth. The gum casts are stored in the casing. Along a gum model of the upper and lower gum casts, there are a number of holes for receiving the artificial teeth and the deciduous teeth, and the upper and lower gum casts are joined along their back edges by a foldable element providing an angle of rotation in-between. The casing contains a lower chamber where a movable drawer is configured for storing adhesives and artificial teeth. A transparent plate is attached to an upper side of the casing, and at least a pair of magnets are correspondingly embedded in the transparent plate and the top side of the casing, respectively, so that a child's photo can be positioned between the casing and the transparent plate.

15 Claims, 7 Drawing Sheets

DECIDUOUS TEETH STORAGE DEVICE

BACKGROUND OF THE INVENTION (a) Technical Field of the Invention

The present invention is generally related to storage devices, and more particular to devices for storing a child's deciduous teeth after they are replaced by the permanent teeth.

(b) Description of the Prior Art

Deciduous teeth, also known as baby teeth, temporary teeth, milk teeth, are a child's the first set of teeth. They are gradually replaced by permanent teeth during which the child begins to learn to speak. This is a stage full of loving memories of all parents, and the deciduous teeth are often collected as a record of the child's growth.

However, there is no appropriate product for collecting and storing deciduous teeth. They are usually temporarily placed in a corner of a drawer or in a randomly selected container. After a while, the parents may forget where the deciduous teeth are stored.

In addition, even though a dedicated container is reserved for the deciduous teeth, there is no appropriate stand where the deciduous teeth can be placed in accordance with their gum location. The deciduous teeth are usually scattered in the container, and the parents most of the time cannot remember which is front teeth, which is the molar teeth, etc.

SUMMARY OF THE INVENTION

Therefore, a novel deciduous teeth storage device is provided herein. The storage device contains an upper gum cast, a lower gum cast, and a number of artificial teeth. Along a gum model of the upper and lower gum casts, there are a number of holes for receiving the artificial teeth and the deciduous teeth, and the upper and lower gum casts are joined along their back edges by a foldable element providing an angle of rotation in-between. The deciduous teeth therefore can be orderly stored in the holes of the gum casts according to their gum locations for convenient observation.

Before the deciduous teeth are stored, artificial teeth are placed in the holes to prevent dust from accumulating in the holes. To store the deciduous teeth, the correspondingly located artificial teeth are first removed the holes, and the deciduous teeth are embedded in the emptied holes.

The storage device further contains an openable casing where the upper and lower gum casts are housed. The casing contains a box and a foldable cover connected to the box. The box contains a lower chamber for storing related objects such as adhesives for gluing the deciduous teeth to the holes, USB drives where a child's photos are stored. The storage device therefore provides not only protection to the deciduous teeth, but also storage for related objects.

The casing can be made of a transparent material so that the gum casts and the collected deciduous teeth are clearly visible from the outside. A user can easily recognize where the deciduous teeth are stored. The orderly arrangement of the deciduous teeth, along with the gum casts, in the transparent casing provides enhanced visual appearance for all the memorable moments.

Furthermore, the gum casts can be manufactured in accordance with the average gum sizes of children during permanent teeth growth period of different areas. The gum casts therefore are suitable for children of different areas. The storage device also provides an adhesive for adhering the deciduous teeth plugged into the holes of the gum casts so that the deciduous teeth are reliably fixed to the gum casts. The adhesive can be amorphous wax, hot melt glue, polyurethane (PU), or silicone.

The upper and lower gum casts can be made by a wide selection of materials such as polyurethane (PU), plastics, and silicone.

A transparent plate is attached to an upper side of the casing, and at least a pair of magnets are correspondingly embedded in the transparent plate and the top side of the casing, respectively, so that a child's photo can be positioned between the casing and the transparent plate.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
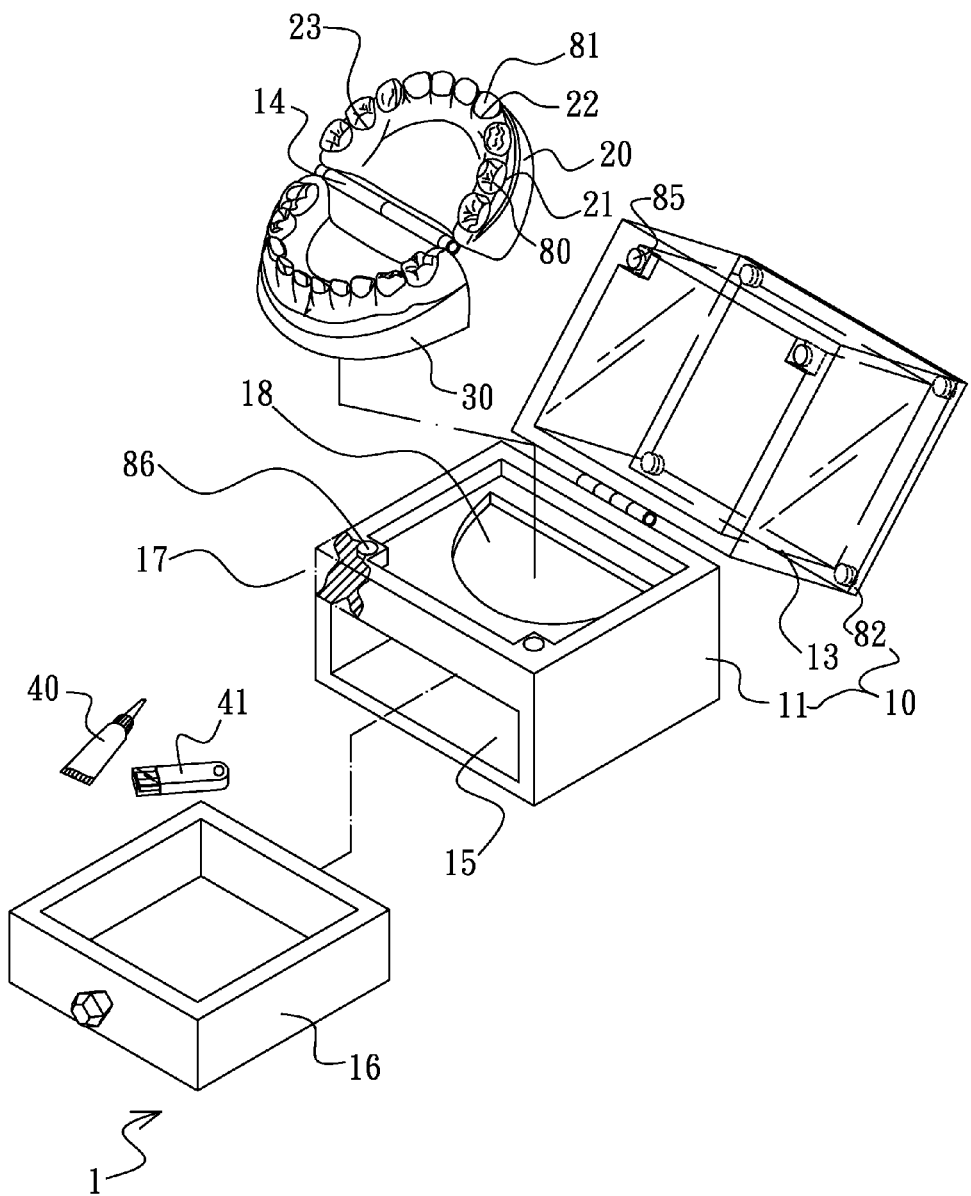
FIG. 1 is a perspective break-down diagram showing the various components of a deciduous teeth storage device according to an embodiment of the present invention.
Figure 2:
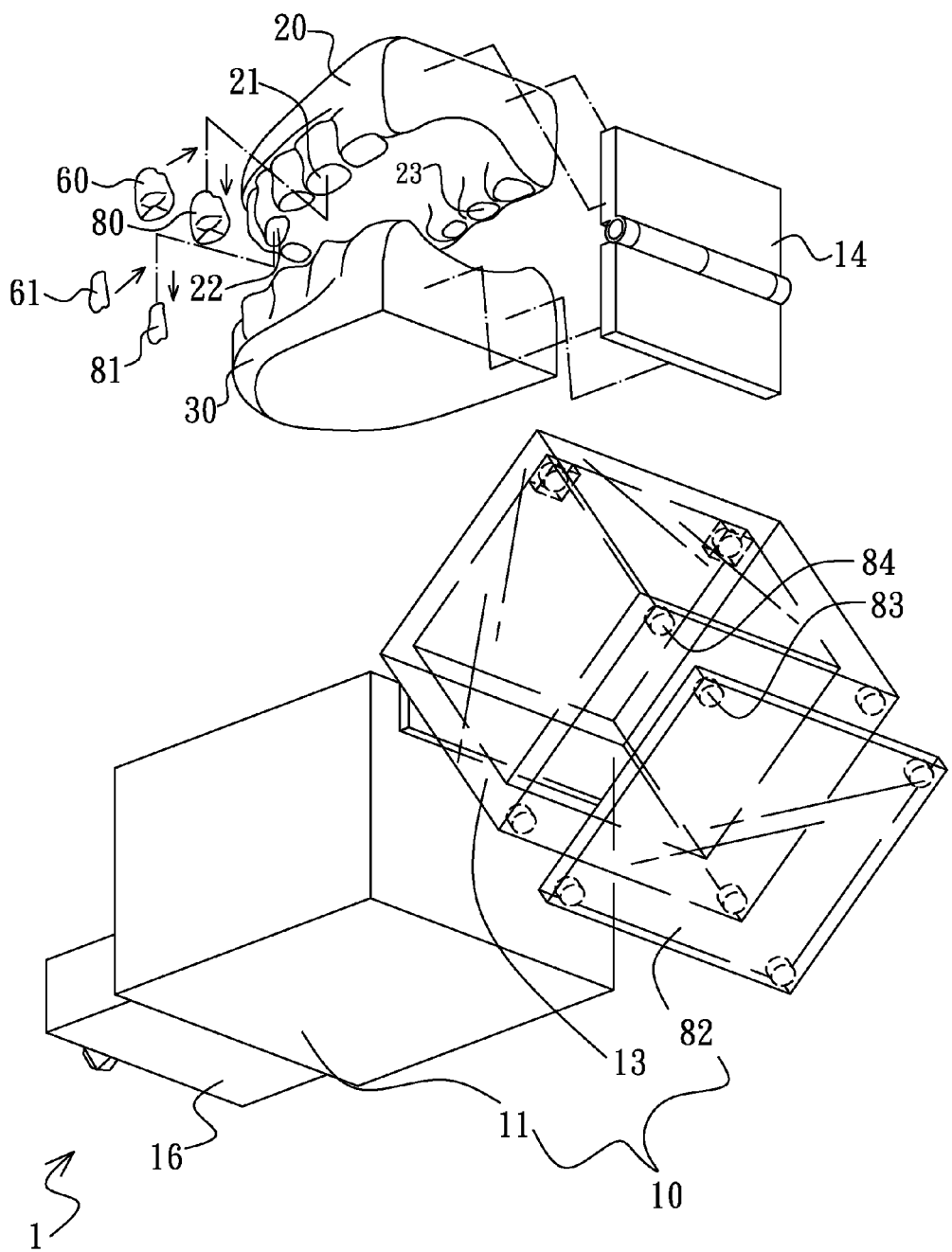
FIG. 2 is another perspective break-down diagram showing the various components of the deciduous teeth storage device of FIG. 1.
Figure 3:
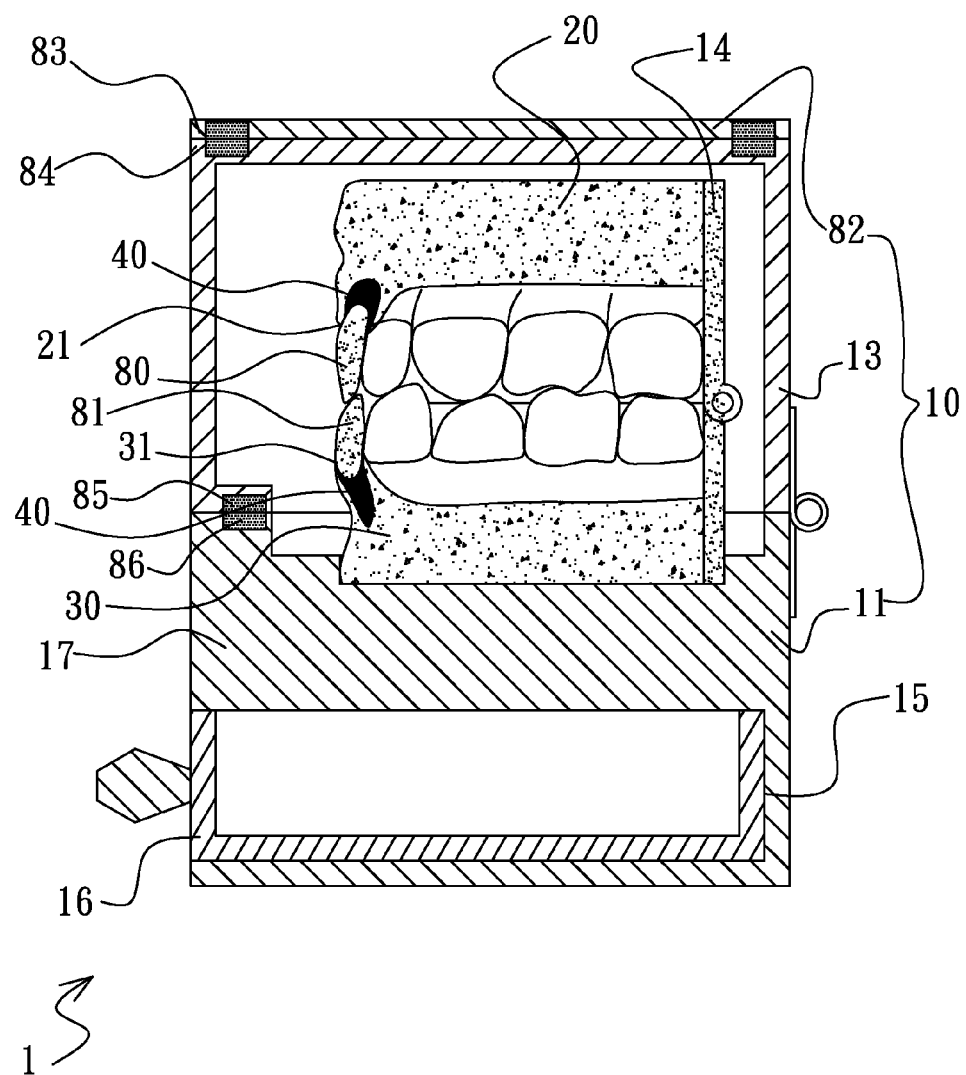
FIG. 3 is a schematic sectional diagram of the deciduous teeth storage device of FIG. 1.

FIG. 1 is a perspective break-down diagram showing the various components of a deciduous teeth storage device 1 according to an embodiment of the present invention. FIG. 2 is also a perspective break-down diagram but from a different viewing angle. FIG. 3 is a sectional diagram. As illustrated, the deciduous teeth storage device 1 contains a casing 10, an upper gum cast 20, a lower gum cast 30, and a number of artificial teeth 80, 81. Along a gum model of the upper and lower gum casts 20 and 30, there are holes 21, 22, 23 for receiving the stored deciduous teeth. The upper and lower gum casts 20 and 30 are joined along their back edges by a foldable element 14 such as a hinge, allowing an angle of rotation between the upper and lower gum casts 20 and 30. The casing 10 contains a box 11 and a cover 13 also connected by a foldable element along their back edges. The box 11 contains a partition 17 separating a lower chamber 15 from the box 11 where a drawer 16 is movably configured. The drawer 16 is for storing an adhesive 40, a USB drive where a child's photos are stored, and so on. An upper side of the partition 17 is configured with an indentation 18 whose shape is compatible to that of the lower gum cast 30 but the former is slightly larger than the latter. The lower gum cast 30 therefore can be embedded into the indentation 18 while the upper gum cast 20 is still hinged with lower gum cast 20. The casing 10 is made of a hard plastic material which can be transparent or opaque. The upper and lower gum casts 20 and 30 are made of one of polyurethane (PU), plastics, or silicone. The adhesive 40 can be one of amorphous wax, hot melt glue, PU, or silicone. Each hole 21, 22, 23 is filled with artificial teeth 80 or 81 so as to provide better appearance and to prevent dust from accumulating in the holes 21, 22, 23 before a deciduous tooth is placed in the hole. A transparent plate 82 can be flatly attached to an upper side of the cover 13. Magnets 83 and 84 of reversed polarities are correspondingly embedded at appropriately places on the transparent plate 82 and a top side of the cover 13, respectively. The purpose of the magnets 83 and 84 will be explained later.

Along the cover 13's a front bottom edge and the box 11's a front upper edge, magnets 85 and 86 of reversed polarities are correspondingly embedded, respectively, so that the cover 13 closes the box 11 more reliably.

As shown in FIG. 3's sectional view, adhesive 40 can be injected into the holes 21 and 31 along the upper and lower gum casts 20 and 30 so that artificial teeth 80, 81 and deciduous teeth 60, 61 (see FIG. 2) can be reliably retained in the holes 21 and 31.

Figure 4:
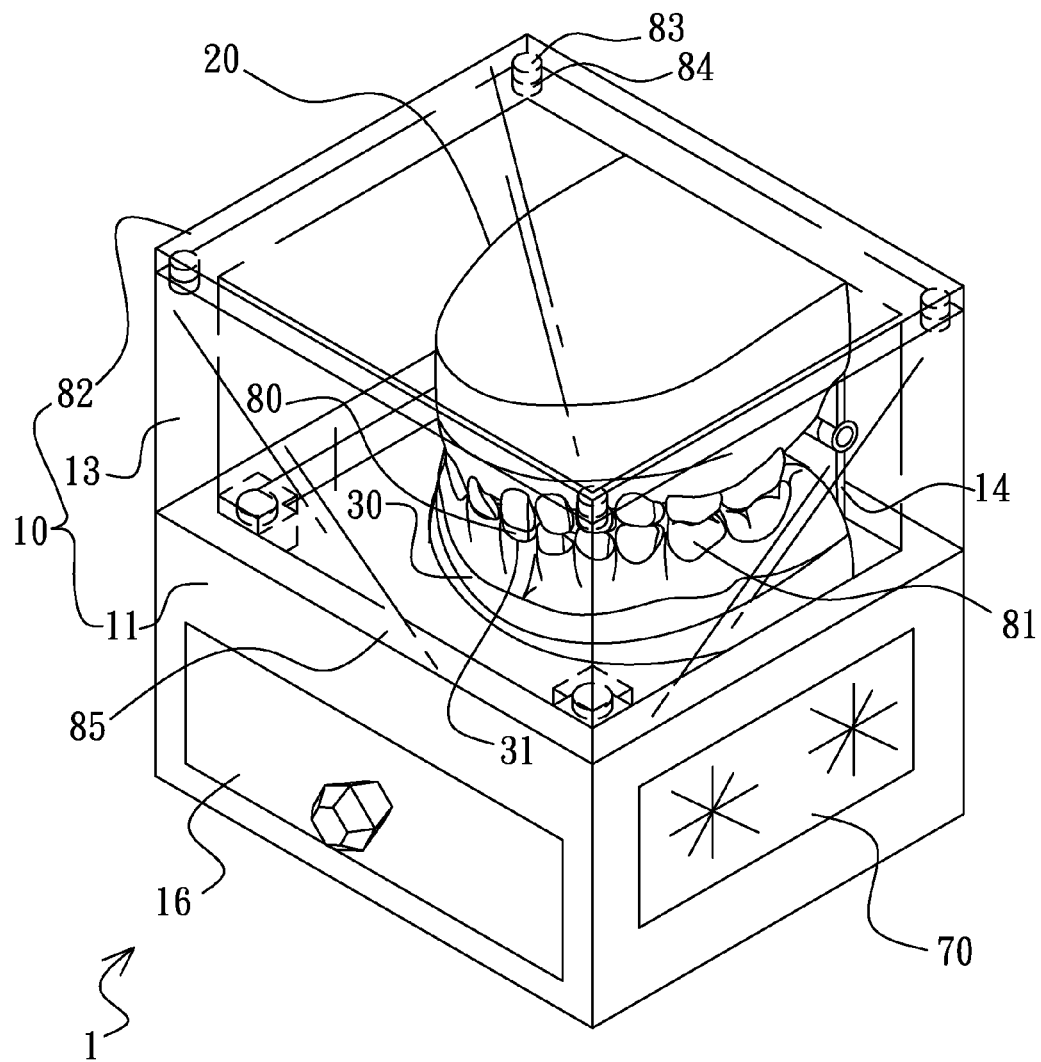
FIG. 4 is a perspective diagram showing a deciduous teeth storage device according to another embodiment of the present invention.

FIG. 4 is a perspective diagram showing a deciduous teeth storage device according to another embodiment of the present invention where the entire cover 13 is transparent.

Figure 5:
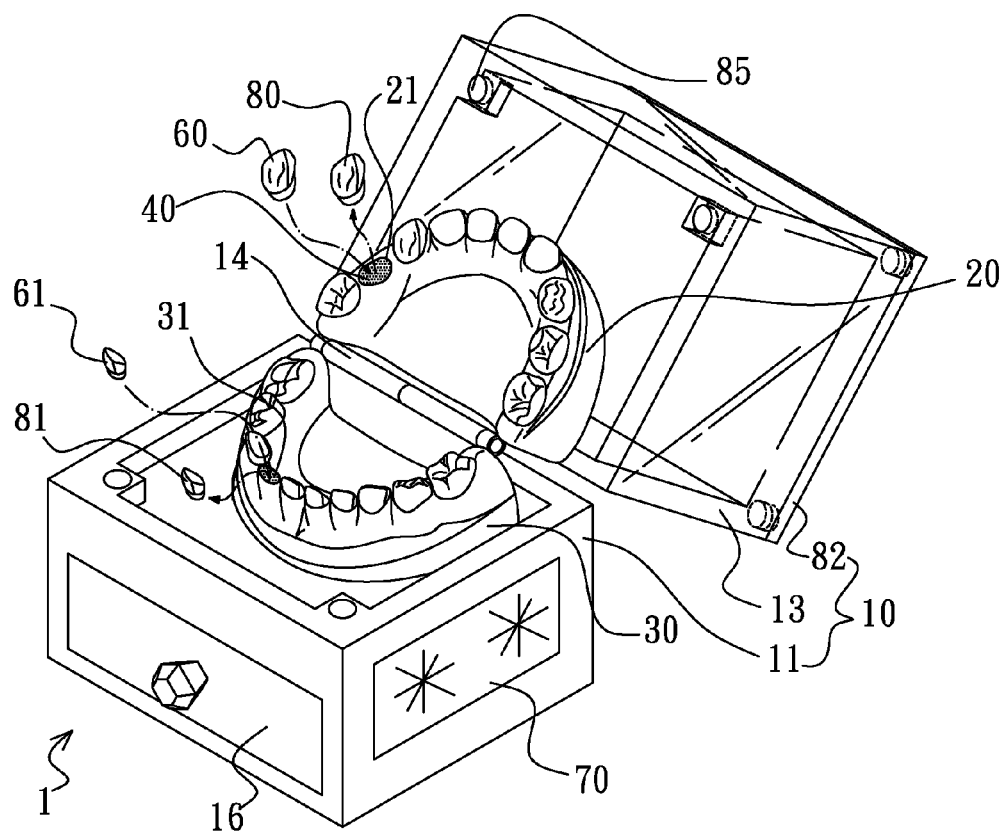
FIG. 5 shows an application scenario of the deciduous teeth storage device of FIG. 4.
Figure 6:
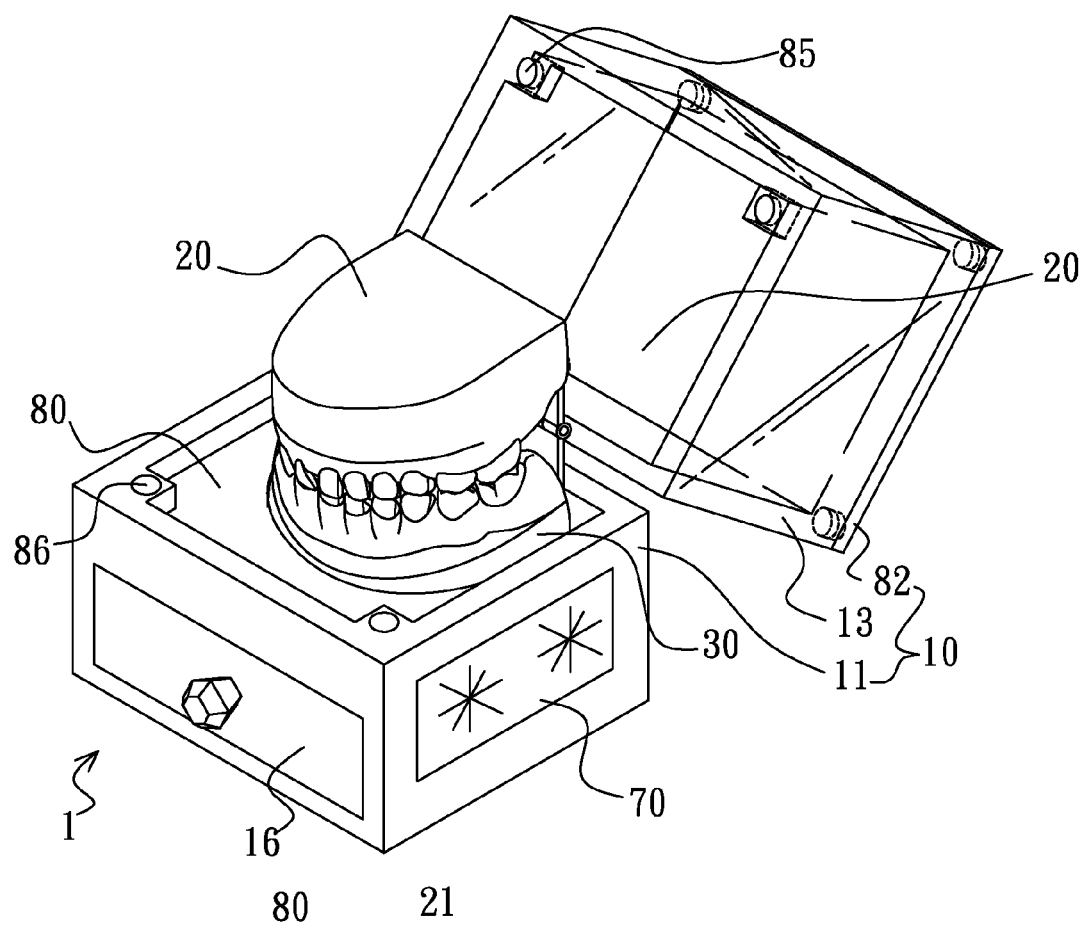
FIG. 6 shows another application scenario of the deciduous teeth storage device of FIG. 4.
Figure 7:
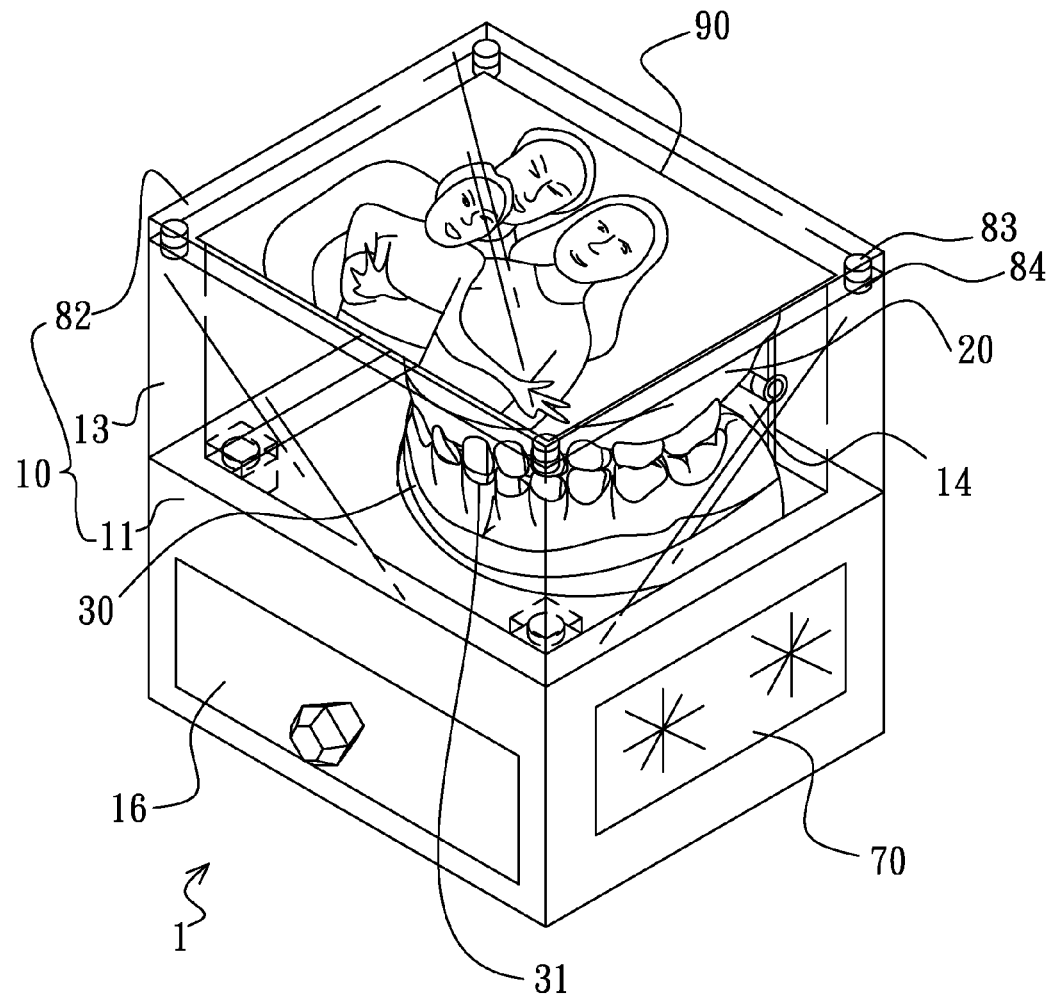
FIG. 7 shows yet another application scenario of the deciduous teeth storage device of FIG. 4.

As shown in FIGS. 5 to 7, which are application scenarios of the present embodiment, a top side of the upper gum cast 20 is first revealed when the cover 13 is opened. Then, to store a deciduous tooth 60, the upper gum cast 20 is opened, and an artificial tooth 80 at the corresponding location to the deciduous tooth 60 is removed. Adhesive 40 is filled in a hole 21 revealed by the removal of the artificial tooth 80, and the deciduous tooth 60 is embedded in the hole 21. A next deciduous tooth 61 is stored in the same way as described above. Finally, the upper gum cast 20 and the cover 13 are closed. Additionally, a note 70 specifying such as the name of the child can be attached to an inner or outer wall of the casing 10. A sheet of information 90 such as the child's photo, drawing, or birth certificate can be positioned between the cover 13 and the transparent plate 82. The magnets 83 and 84 allows the transparent plate 82 to be easily and conveniently detached and restored.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A storage device for storing deciduous teeth comprising:
an openable casing;
an upper gum cast in the casing;
a lower gum cast in the casing; and
a plurality of artificial teeth;
wherein along a gum model of the upper and lower gum casts, there are a plurality of holes for receiving the artificial teeth and the deciduous teeth; and the upper and lower gum casts are joined along their back edges by a foldable element providing an angle of rotation between the upper and lower gum casts.

2. The storage device according to claim 1, wherein the casing comprises a lower chamber.

3. The storage device according to claim 1, wherein an adhesive is injected in the holes so that the artificial teeth and the deciduous teeth are reliably embedded in the holes.

4. The storage device according to claim 1, wherein the casing comprises a box and a cover connected by a foldable element along their back edges; and the lower gum cast is embedded to an upper side of the box.

5. The storage device according to claim 1, wherein the upper and lower gum casts are made of polyurethane (PU).

6. The storage device according to claim 1, wherein the upper and lower gum casts are made of plastics.

7. The storage device according to claim 1, wherein the upper and lower gum casts are made of silicone.

8. The storage device according to claim 4, wherein the casing is made of a transparent hard plastic material.

9. The storage device according to claim 4, wherein the casing is made of an opaque hard plastic material.

10. The storage device according to claim 3, wherein the adhesive is amorphous wax.

11. The storage device according to claim 3, wherein the adhesive is hot melt glue.

12. The storage device according to claim 1, wherein a transparent plate is attached to an upper side of the casing; a sheet of information is positioned between the casing and the transparent plate; and at least a pair of magnets of reversed polarities are correspondingly embedded in the transparent plate and the top side of the casing, respectively, so that the transparent plate is easily and conveniently detached and restored.

13. The storage device according to claim 4, wherein the upper side of the box is configured with an indentation whose shape is compatible to but slightly larger than that of the lower gum cast; and the lower gum cast therefore is embedded into the indentation while the upper gum cast is hinged with the lower gum cast.

14. The storage device according to claim 2, wherein a drawer is movably configured in the chamber.

15. The storage device according to claim 4, wherein along a front bottom edge of the cover and a front upper edge the box, at least a pair of magnets of reversed polarities are correspondingly embedded, respectively, so that the cover closes the box 11 reliably.

* * * * *